US012290454B2

(12) United States Patent
Nawn et al.

(10) Patent No.: US 12,290,454 B2
(45) Date of Patent: May 6, 2025

(54) DIGITAL EXTENDERS WITH HAPTIC FEEDBACK

(71) Applicant: The Board of Regents of The University of Texas System, Austin, TX (US)

(72) Inventors: Corinne Nawn, San Antonio, TX (US); Carlyn Abbott, San Antonio, TX (US); Caroline Campbell, San Antonio, TX (US); Sarah Robinson, Austin, TX (US); Robert Hood, San Antonio, TX (US); Christian Wahrmund, San Antonio, TX (US); Andrea Afanador, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/755,711

(22) PCT Filed: Oct. 13, 2018

(86) PCT No.: PCT/US2018/055779
§ 371 (c)(1),
(2) Date: Apr. 13, 2020

(87) PCT Pub. No.: WO2019/075443
PCT Pub. Date: Apr. 18, 2019

(65) Prior Publication Data
US 2021/0196482 A1    Jul. 1, 2021

Related U.S. Application Data

(60) Provisional application No. 62/571,911, filed on Oct. 13, 2017.

(51) Int. Cl.
*A61B 34/00* (2016.01)
*A61F 2/56* (2006.01)
(Continued)

(52) U.S. Cl.
CPC .............. *A61F 2/586* (2013.01); *A61B 34/76* (2016.02); *A61F 2/588* (2013.01); *A61F 2/70* (2013.01);
(Continued)

(58) Field of Classification Search
CPC ...... A61F 2002/5058–5063; A61F 2002/6827; B25J 13/025
(Continued)

(56) References Cited

U.S. PATENT DOCUMENTS 3,535,711 A * 10/1970 Fick ...................... A61F 5/0102
901/33
4,302,138 A * 11/1981 Zarudiansky ........... G06F 3/014
414/730
(Continued)

FOREIGN PATENT DOCUMENTS

EP    2 664 302 A2 * 11/2013    ............. A61F 2/583
JP    2004-213350 A *  7/2004    ............. G06F 3/014
(Continued)

OTHER PUBLICATIONS

SU 1662548 A1 (published Jun. 15, 1988; previously cited in the Office action of Oct. 6, 2021): human translation.*
(Continued)

*Primary Examiner* — David H Willse (57) ABSTRACT

Certain embodiments are directed to mechanical devices for augmenting dexterous reach and sensing of a user. The devices can include a proximal portion configured to receive an appendage of a user; a distal portion configured to detect sensory information; an articulation positioned between the proximal and distal portion to provide for motion of the distal portion via manipulation of the proximal portion; wherein the distal portion comprising a sensing element and the proximal portion comprises a feedback element, the
(Continued)

feedback element being connected to the sensing element providing for physical extension of sensory capabilities of the appendage.

11 Claims, 10 Drawing Sheets

(51) Int. Cl.
*A61F 2/58* (2006.01)
*A61F 2/70* (2006.01)
*A61B 1/00* (2006.01)
*A61F 2/50* (2006.01)
*A61F 2/68* (2006.01)
*A61F 2/78* (2006.01)

(52) U.S. Cl.
CPC ..... *A61B 1/00147* (2013.01); *A61F 2002/502* (2013.01); *A61F 2002/5061* (2013.01); *A61F 2002/5063* (2013.01); *A61F 2002/5084* (2013.01); *A61F 2002/6827* (2013.01); *A61F 2002/701* (2013.01); *A61F 2002/7862* (2013.01)

(58) Field of Classification Search
USPC .......................................................... 414/5
See application file for complete search history.

(56) References Cited

U.S. PATENT DOCUMENTS

| | | | |
|---|---|---|---|
| 5,004,391 A | | 4/1991 | Burdea |
| 5,619,180 A | * | 4/1997 | Massimino ............ B25J 9/1689 340/407.1 |
| 6,908,489 B2 | | 6/2005 | Didrick |
| 7,302,296 B1 | | 11/2007 | Hoffer |
| 2008/0200994 A1 | | 4/2008 | Colgate et al. |
| 2008/0288088 A1 | | 11/2008 | Langenfeld et al. |
| 2015/0230941 A1 | | 8/2015 | Jury |
| 2016/0213978 A1 | | 7/2016 | Ban et al. |
| 2017/0348117 A1 | * | 12/2017 | Strbac ...................... A61F 2/72 |

FOREIGN PATENT DOCUMENTS

| | | | | |
|---|---|---|---|---|
| KR | 10-2018-0106346 A | * | 10/2018 | ............. A61F 2/586 |
| SU | 1662548 A1 | * | 7/1991 | ............... A61F 2/56 |

OTHER PUBLICATIONS

"MCPDrivers Used to Button Shirt Cuff" Naked Prostetics, Feb. 8, 2017, URL <https://www.youtube.com/watch?c=zvwny19dWGA.
"Mechanical hands finger extensions" Farche, Sep. 14, 2009, URL <https://www.youtube.com/watch?v=EcJZOFwKY5Q >.
"Palpation" Wikipedia, Jul. 31, 2017, URL < https://en.wikipedia.org/wiki/palpation.
International Search Report and Written Opinion issued in corresponding International Patent Application No. PCT/US2018/055779, dated Dec. 31, 2018.

* cited by examiner

DIGITAL EXTENDERS WITH HAPTIC FEEDBACK

CROSS REFERENCE TO RELATED APPLICATIONS

This application is a national phase under 35 U.S.C. § 371 of International Application No. PCT/US2018/055779, filed Oct. 13, 2018, which claims priority to U.S. Provisional Patent Application Ser. No. 62/571,911, filed Oct. 13, 2017, the entire contents of each of which are incorporated herein by reference in their entirety.

STATEMENT REGARDING FEDERALLY FUNDED RESEARCH

None.

BACKGROUND OF THE INVENTION

A. Field of the Invention

The invention generally concerns a device or apparatus for extending the natural physical reach and tactile capabilities of a subject. In particular the device or apparatus includes a distal tactile sensor in communication with a subject's appendage.

B. Description of Related Art

Biomedical devices and instruments serve many purposes-often aiding in sensing or manipulating physiology beyond natural human capabilities. Medical instruments, especially those for surgical applications, are designed to provide an extension to the provider's dexterous control in a specialized design form customized to the procedure at hand. This has given rise to a myriad number of surgical instruments as a function of the highly delicate and specialized procedures surgeons perform. However, these specialized instruments limit the surgeon's innate dexterous manipulation and sensing. Thus, physicians still commonly use their sense of touch to perform a number of medical procedures or diagnostics; however, their scope is inherently limited by the size and length of their digits. Additionally, utilizing their digits to perform certain tasks could introduce risk to the patient, such as infection, or the provider could put his or her own digits at risk, such as in digital intubation where the provider places his or her digits in a patient's mouth to secure the airway.

SUMMARY OF THE INVENTION

The digital extenders platform with haptic feedback may be used to extend the mechanical and sensory reach of a natural digit. The device includes a mechanical platform to translate and replicate motion from the wearer's natural digit to that of the extended mechanical digits. The distal mechanical digit includes a sensory component to detect the distal environment and translate the sensory information to the natural digit. This sensory information may include tactile, pressure, temperature or other signals that transmit meaningful feedback to the user about the distal environment. This device may be used to palpate structures in medical scenarios or austere environments where desired dexterous control and feel are out of reach or unsafe for natural digits.

Certain embodiments are directed to mechanical devices for augmenting dexterous reach and sensing of a user. The devices can include a proximal portion configured to receive an appendage of a user; a distal portion configured to detect sensory information; an articulation component to provide for motion of the distal portion via manipulation of the proximal portion; wherein the distal portion comprising a sensing element and the proximal portion comprises a feedback element, the feedback element being connected to the sensing element providing for physical extension of sensory capabilities of the appendage.

In certain aspects the sensing element is a thermal, capacitive, hydraulic, resistive, and/or piezoelectric sensing element. The device can be configured to translate movement of an appendage to movement of the distal portion. In certain aspects the translation is scaled at a scale of 1000:1, 500:1, 100:1, 10:1 to 1:1 to 1:10, 1:100, 1:500, 1:1000 proximal distance moved to distal distance moved. The proximal portion can be configured to encapsulate a portion of the appendage. In certain aspects the device can be coupled to an attachment mechanism to secure the device to a user. The attachment mechanism can be a glove or sleeve or sock or strap worn by the user.

The device can be made of or include materials that are capable of being sterilized. In certain aspects the digital extender portion of the device can be up to, at least, or about 1, 2, 3, 4, 5, 6, 7, 8, 9, 10, 11, 12, 13, 14, 15, 16, 17, 18, 19, 20, 21, 22, 23 to 24 inches long, including all values and ranges there between, 4 to 10 inches in certain embodiments. Embodiments of the extender digit can have a maximum cross section of up to, at least, or about 0.5, 1, 2 to 3, 4, 5 cm. In other aspects the extender digit can have a minimum cross section of up to, at least, or about 0.01, 0.1, 1 to 2, 3, 4 cm. In certain embodiments and based on intended use the device is a medical device.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa.

The use of the word "a" or "an" when used in conjunction with the term "comprising" in the claims and/or the specification may mean "one," but it is also consistent with the meaning of "one or more," "at least one," and "one or more than one."

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are defined to include ranges within 10%, within 5%, within 1%, or within 0.5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing"

(and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein. In the drawings, which are not necessarily to scale, like or corresponding parts are denoted by like or corresponding reference numerals.

FIG. 5A-5F illustrates another embodiment directed to a two digit, actuate digital extender device.

DETAILED DESCRIPTION OF THE INVENTION

Certain embodiments of the invention provide a physical extension to the fingers (digits) or other appendages while also providing a degree of tactile sensing (haptic feedback) and movement control. Haptic feedback currently exists in robotics technology and within the biomedical engineering field, as a part of robotic surgeries. Most of the current technology investigating haptic feedback or artificial limbs endeavors to replace missing digits or mimic the sensory and kinematic components of fingers for robotic applications.

Certain configurations are designed to work with fully functioning biological digit(s), serving as an extension of a fully functioning digit(s), particularly for biomedical applications. Certain embodiments of a device or apparatus described herein provides a user an extension of their fingers, approximately 4 to 10 inches, in order to extend his or her digital feel and control, possibly for purposes such as performing medical procedures or palpations. Currently, clinical providers use a myriad of medical devices or probes to visualize or manipulate patient anatomy for medical procedures. Digital extenders allow the provider to both locate and treat pathologies through palpation and manipulation without the need for switching tools or imaging.

The digital extenders platform with haptic feedback may be used to extend the mechanical and sensory reach of a natural digit. The device includes a mechanical platform to translate and replicate motion from the wearer's natural digit to that of the extended mechanical digits. The distal mechanical digit includes a sensory component to detect the distal environment and translate the sensory information to the natural digit. This sensory information may include tactile, pressure, temperature or other signals that transmit meaningful feedback to the user about the distal environment. This device may be used to palpate structures in medical scenarios or austere environments where desired dexterous control and feel are out of reach or unsafe for natural digits. As used herein a tactile sensor generally refers to a sensor that creates an electrically or physically (e.g., pressure, etc.) usable signal from pressure or force generated by contact with objects. Some tactile sensors provide limited information, detecting only whether contact above some threshold force or pressure has been made. Others provide detailed spatial measurements, and can be used to determine the location and magnitude of a force applied to a surface, or to estimate the force and torque applied to a rigid body in contact with several tactile sensors (such as the force and torque exerted on the ground by the sole of a foot). A number of such sensors are known in the art and can be adapted for the purposes described herein. Several modalities for tactile sensing and haptic feedback have been developed and procured involving the translation of sensory input to feedback output through mechanisms such as mechanical actuation, microfluidics, and pneumatics as well as electromechanical systems such as capacitive and resistive technologies. Many of the technologies are readily available on the appropriate scale of the proposed digital extenders platform and could be employed in various implementations according to the environmental constraints or desired functionality.

Figure 1:
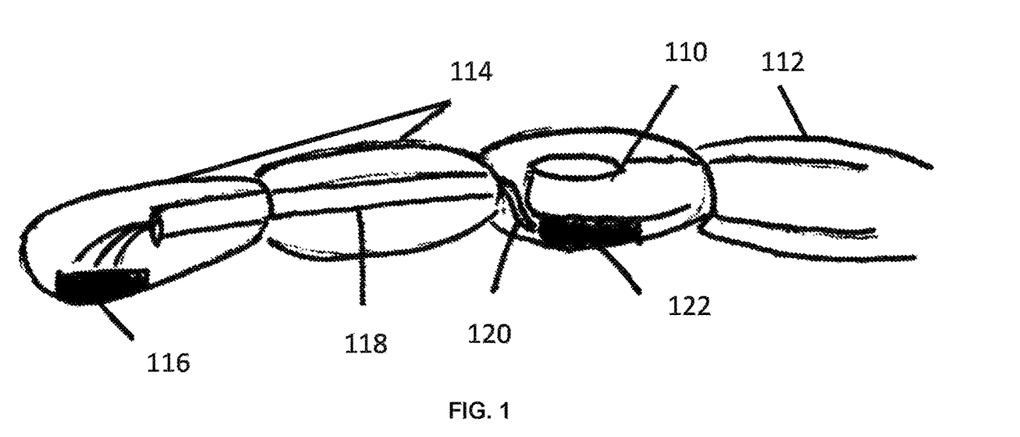
FIG. 1 shows one embodiment of the digital extenders with haptic feedback construct.

FIG. 1 shows one example of a digit extender. The digit extender is an elongated device having a proximal end configured to interact with a user's appendage and a distal end configured to provide tactile information to the user. In the particular example illustrated in FIG. 1, the appendage is a finger or fingertip; however, in other embodiments the appendage can be a hand, palm, toe, or foot. The device can be configured to attach directly to the appendage or can be attached to or incorporated in glove, sleeve, sock, strap, or similar article that is worn by the user.

Referring to FIG. 1, the user places digit 110 in proximal end 112 of the device. The proximal end of the device is configured to fasten digit 110, or other appendage, from the first, second or third knuckle or articulation of the finger or other appendage. In a particular aspect the proximal end of the device covers the distal two knuckles. The fingertip or sensing portion of the appendage can be positioned on haptic feedback element 122. In certain aspects the device has a fixed length. In other aspects the length of the device is adjustable and can be lengthened or shortened by the user. The length of the device can be 1, 2, 3, 4, 5, 6, 7, 8, 9, 10 to 11, 12, 13, 14, 15, 16, 17, 18, 19, 20 inches long, including all values and ranges there between, as measured from proximal end to distal end. In certain embodiments the device is 4 to 10 inches in length. The device can be circular, oval, triangular, square or polygonal solid, matrix, or tube. The solid, matrix, or tube need not maintain a consistent cross section and constrict and expand in circumference or analogous dimension along its length. The proximal end can be flattened and the appendage placed upon the proximal end and affixed to the appendage or the proximal end can be configured to receive the appendage inside the proximal end of the device where it is secured once the appendage is appropriately positioned.

A distal portion 114 extends from the fingertip providing a fingertip extension portion. The distal finger extension has tactile or pressure sensing element 116 that is connected to haptic feedback element 122 and can transmit a sensed signal through connection 118 to haptic feedback element 122 that interfaces with the user's finger or other appendage. Sensing element 116 can use various mechanisms or combination of mechanisms for sensing, including but not limited to thermal, capacitive, hydraulic, or piezoelectric technologies that sense the environment at the distal end of the device (thus physically extending the sensory capability of the user) and translate a meaningful feedback signal to the user's finger that is connected to feedback element 122. The connection between sensing element 116 and feedback element 122 can be a wired or a wireless connection. In certain aspects the device can be moved and/or articulated by the user moving the appendage on which the device is placed or by other manipulation of the device, e.g., dials, gears, wires and such that can be manipulated by a user using an appendage not directly connected to the appendage positioned in the device. The device can have 1, 2, 3, or more articulation points at various lengths along the device. The articulation points can be configured to move in 1, 2, or 3 dimensions, with a first dimension being extension/retraction (x axis), a second dimension being up/down (y axis), and a third dimension being side to side (z axis). One or more articulation joints can be positioned proximal to the distal portion, the articulation joints can provide sufficient flexibility to the distal portion of the device such that the distal portion can be directed over a required deflection range (180° or more) by the steering mechanism and can be directed to bend in any direction desired about the circumference of the distal portion. In certain aspects the user can select both the amount of bend or articulation and the direction of the bend.

Figure 2A:
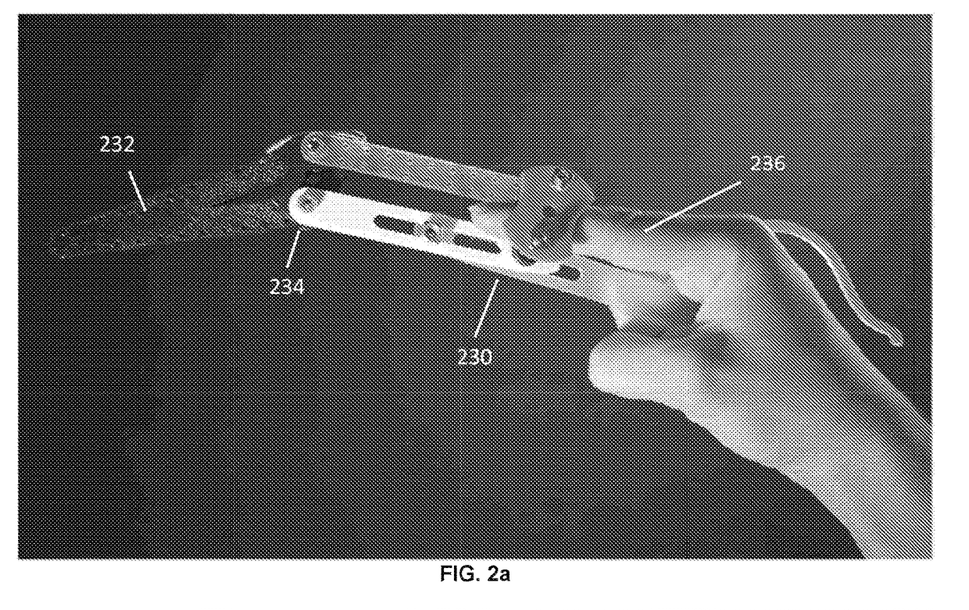
FIGS. 2a and 2b show one embodiment of one kinematic control system for the mechanical platform in an extended and a flexed position.
Figure 2B:
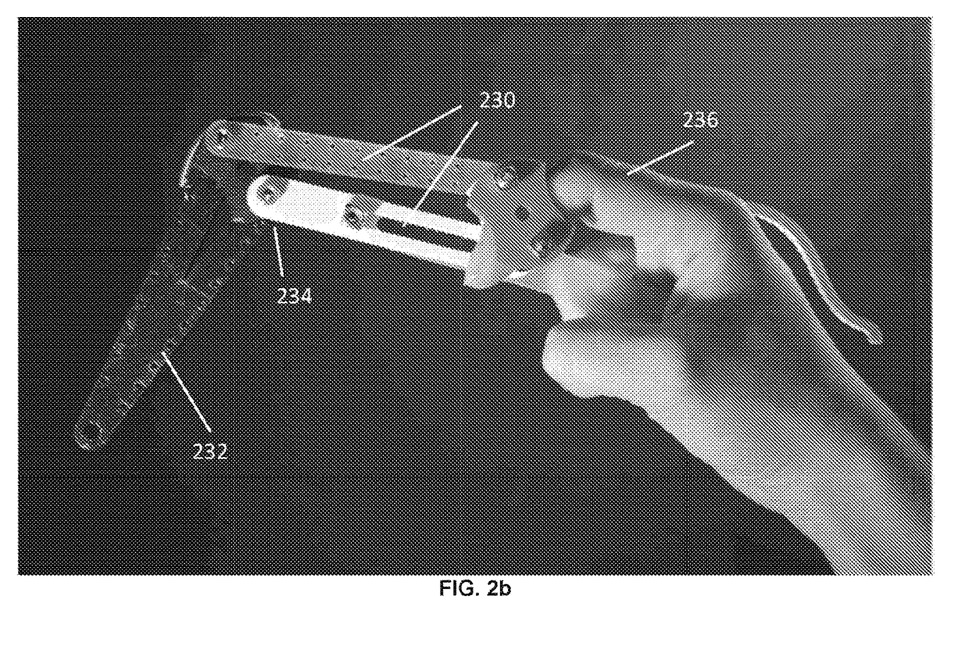

FIG. 2 shows one example of a kinematic control system for the mechanical platform in an extended position (FIG. 2a) and in a flexed position (FIG. 2b) where the flexion and extension of the user's natural digit corresponds to the flexion and extension of the distal mechanical segment or portion 232. Referring to FIG. 2a and FIG. 2b, the mechanical platform has proximal portion 230 and a distal portion 232 that are connected by an articulation 234. The appendage (finger) 236 is shown operatively positioned and affixed to proximal portion 230. Proximal portion 230 is shown having a fixed arm and a moveable arm to allow for movement of distal portion 232 in relation to proximal portion 230 using articulation 234.

Figure 3A:
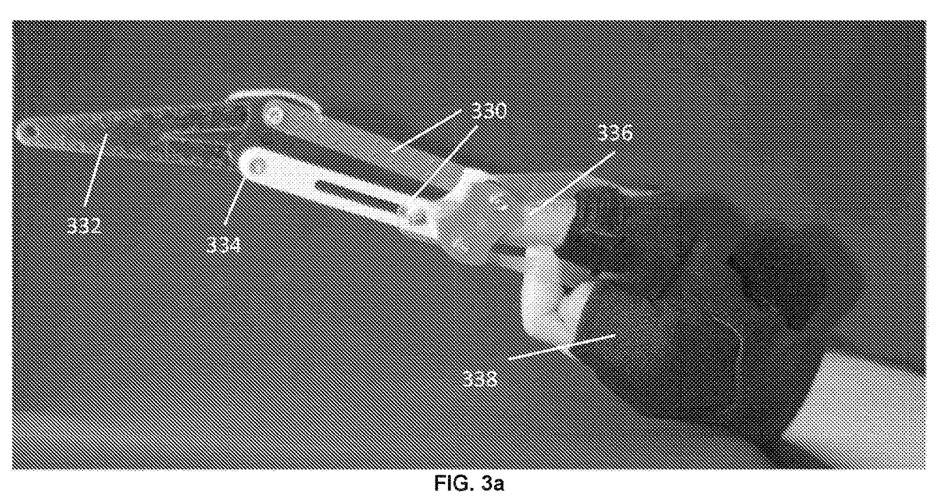
FIGS. 3a and 3b shows another embodiment of the mechanical system where the proximal stabilization of the proposed invention is incorporated into a glove-like format.
Figure 3B:
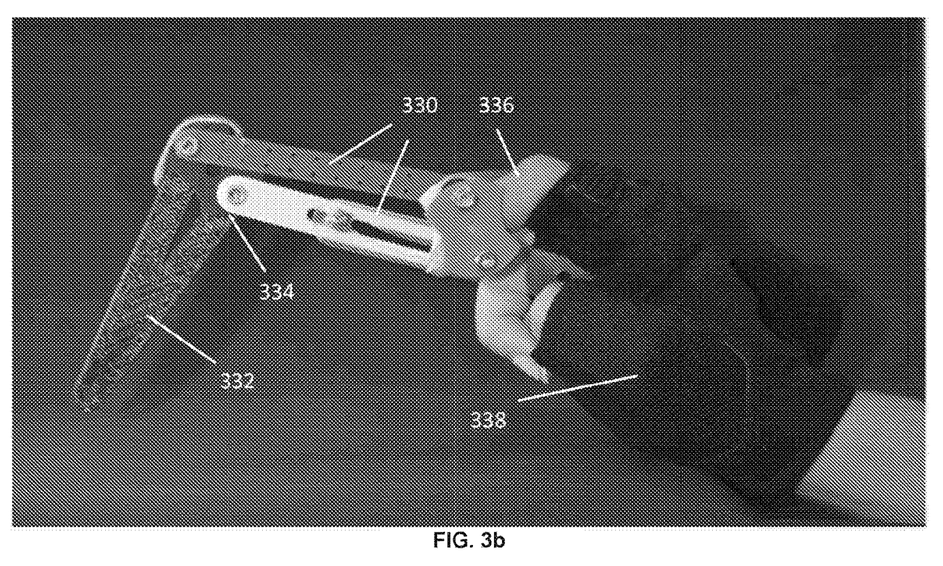

FIG. 3 shows another embodiment of the mechanical system where the proximal stabilization of the proposed invention is incorporated into glove 338. The embodiment is pictured in extension (FIG. 3a) and flexion (FIG. 3b). Other embodiments may include a glove or sleeve element that extends and encloses the user's finger or other appendage and/or the distal mechanical segments partially or entirely.

Figure 4A:
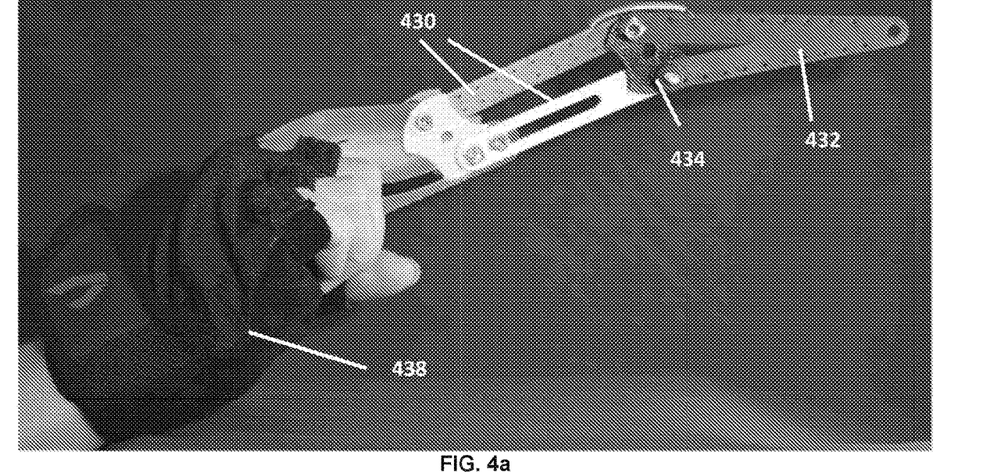
FIGS. 4a and 4b shows one embodiment from a posterior view to display the mechanical translation of the user's digital movement to that of the distal joint for both extension and flexion.
Figure 4B:
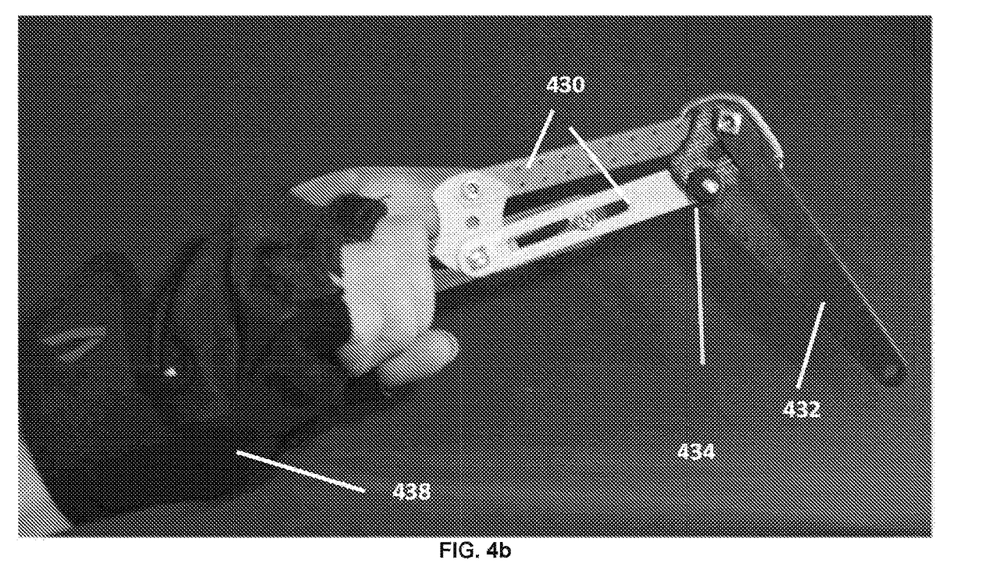

FIG. 4 shows the embodiment of FIG. 3 from a posterior view to display the mechanical translation of the user's digital movement to that of the distal joint for both extension (FIG. 4a) and flexion (FIG. 4b). In one such embodiment, the movement of the user's digit is captured by a proximal mechanical construct and translated to the distal mechanical actuation component. Constant tension may be applied above or below the distal actuation component to aid in overcoming forces for extension or flexion. This may be implemented tension components such as pulleys, spring or elastic materials.

FIG. 5A-5F shows another embodiment of a digit extender having mount portion 540 at the proximal end and finger mount portion 541, with the digits or finger extension(s) 510 connected to finger mount 541 portion. The device that can have one, two, three, or four digits (or finger extensions). The embodiment of FIG. 5 is a two digit configuration with the digits (510a and 510b) of the device corresponding to the index finger 510a and the middle finger 510b of a user. The device has a proximal end 512 configured to interact with an users appendage and a distal end 514, which can be configured to provide tactile information to the user. In the particular example illustrated in FIG. 5, the appendage is a hand; however, in other embodiments the appendage can be a palm, wrist, toe, or foot. The device can be configured to attach directly to the hand via mount portion 540 or can be attached to or incorporated in glove, sleeve, sock, or similar article that is worn by the user.

Figure 5A:
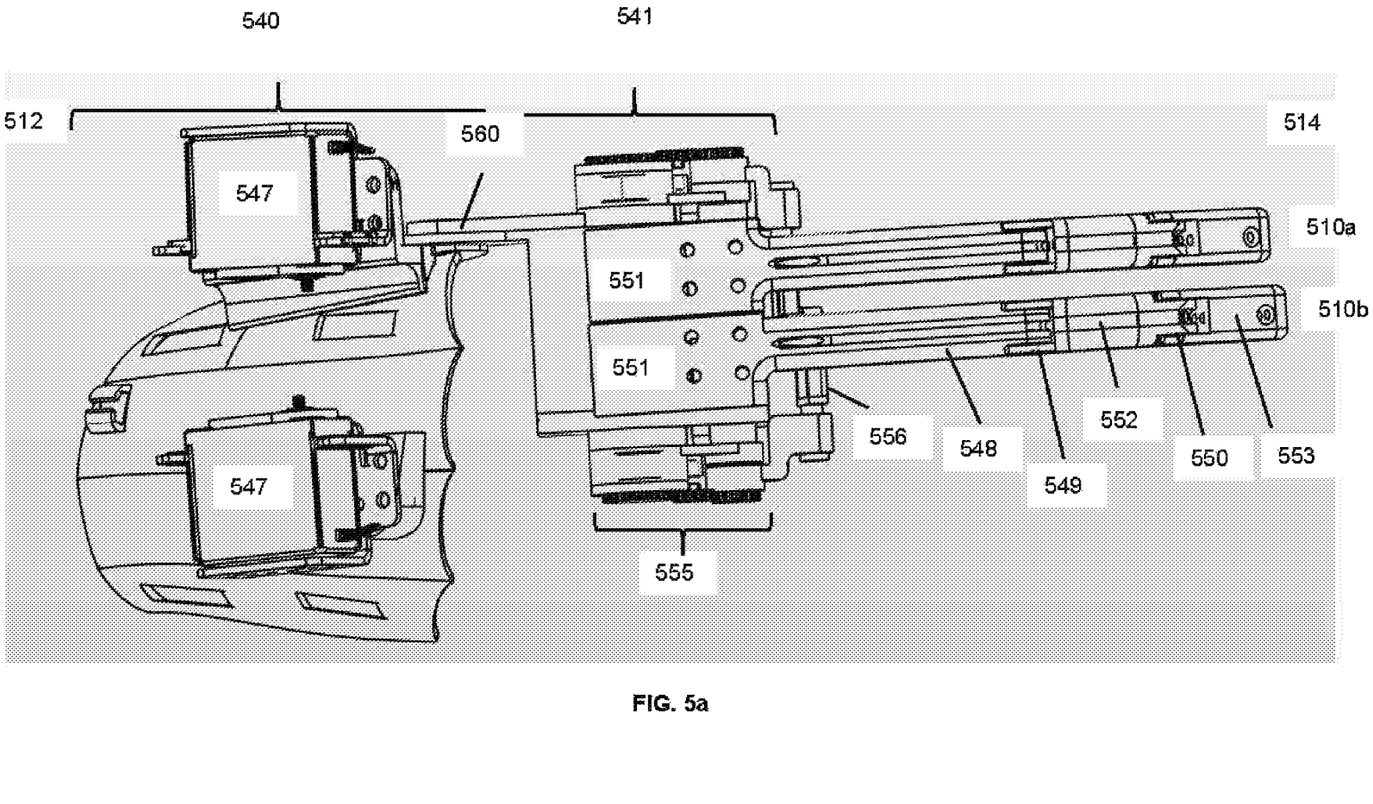
FIG. 5A is a top view.
Figure 5B:
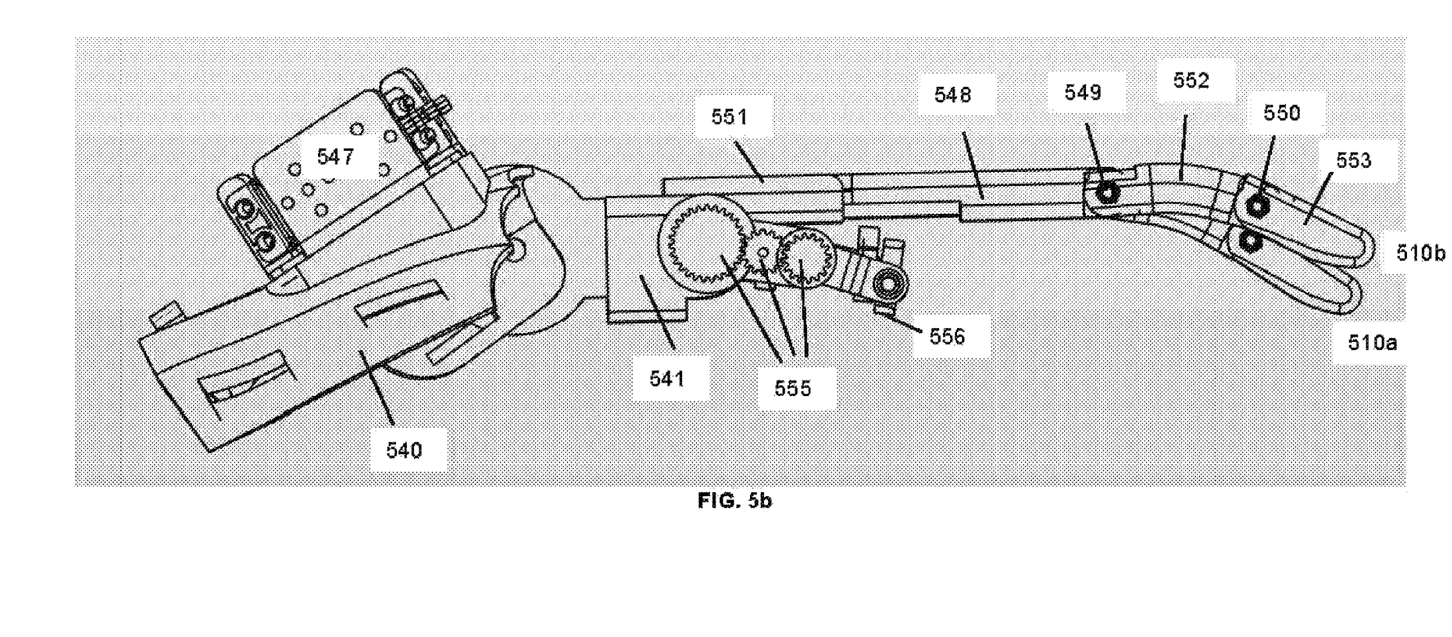
FIG. 5B is a first side view.
Figure 5C:
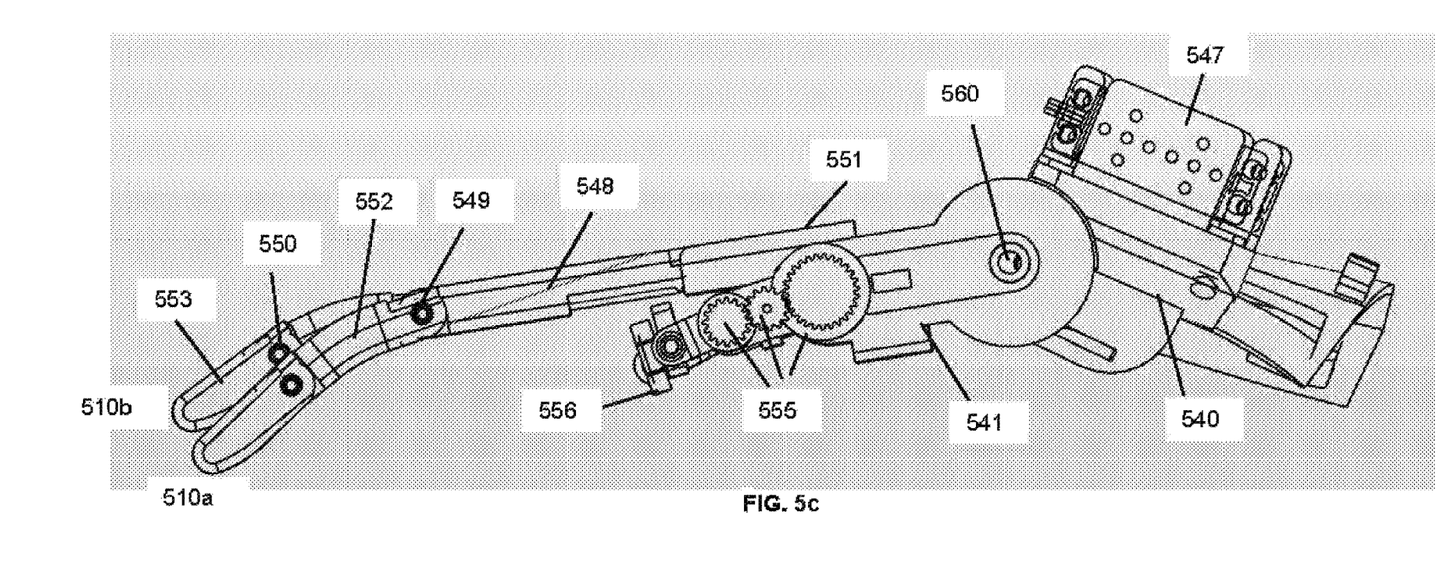
FIG. 5C is a second side view of the embodiment.
Figure 5D:
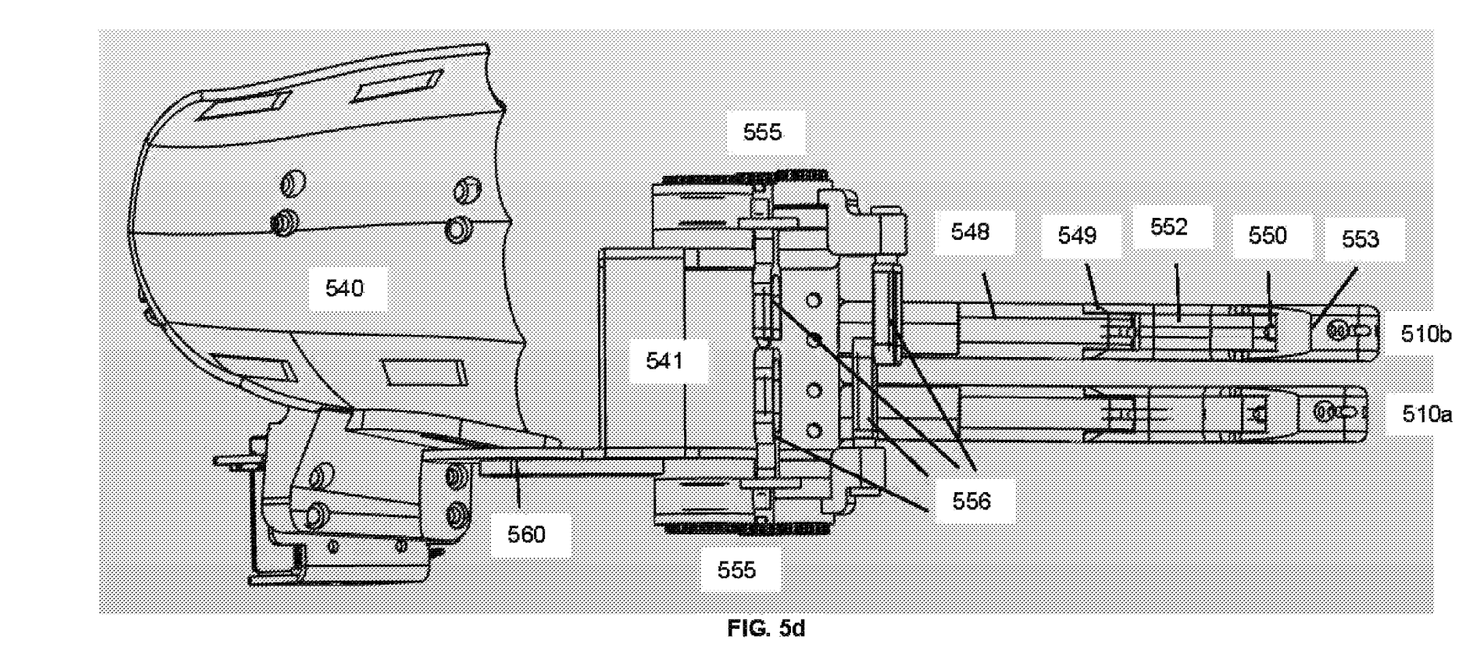
FIG. 5D is a bottom view of the embodiment.
Figure 5E:
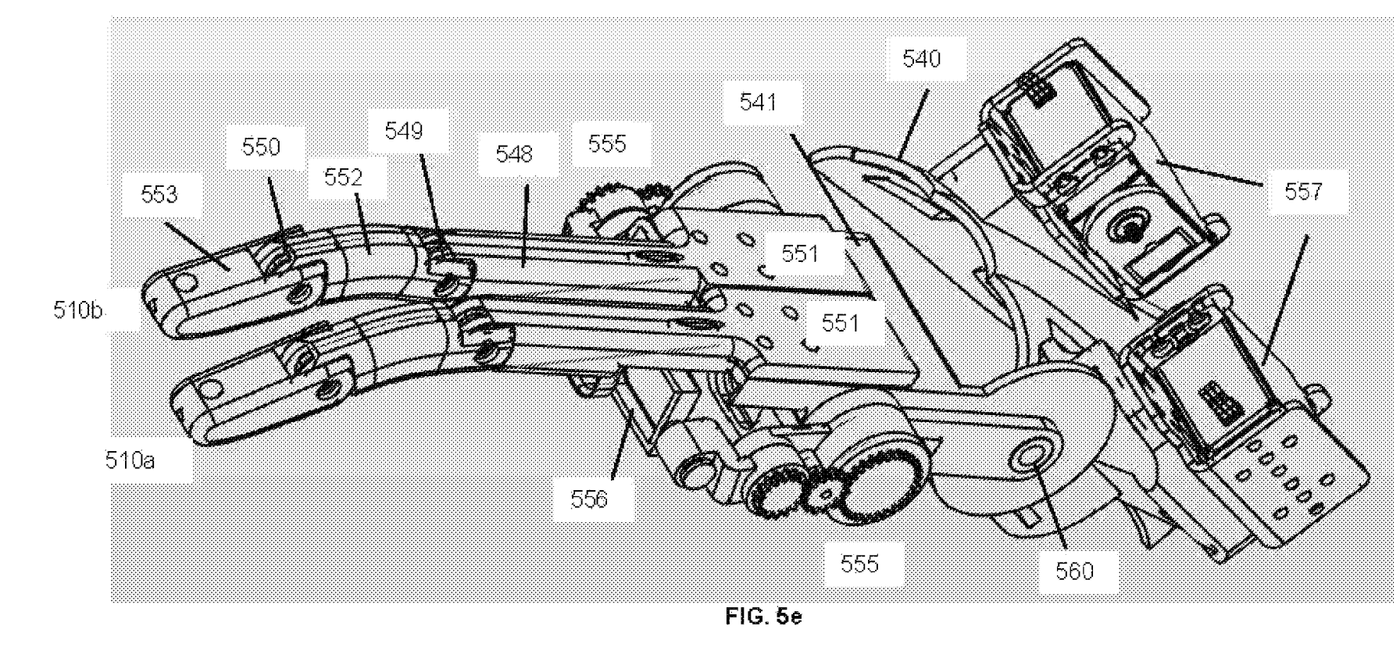
FIG. 5E is a top perspective view of the embodiment.
Figure 5F:
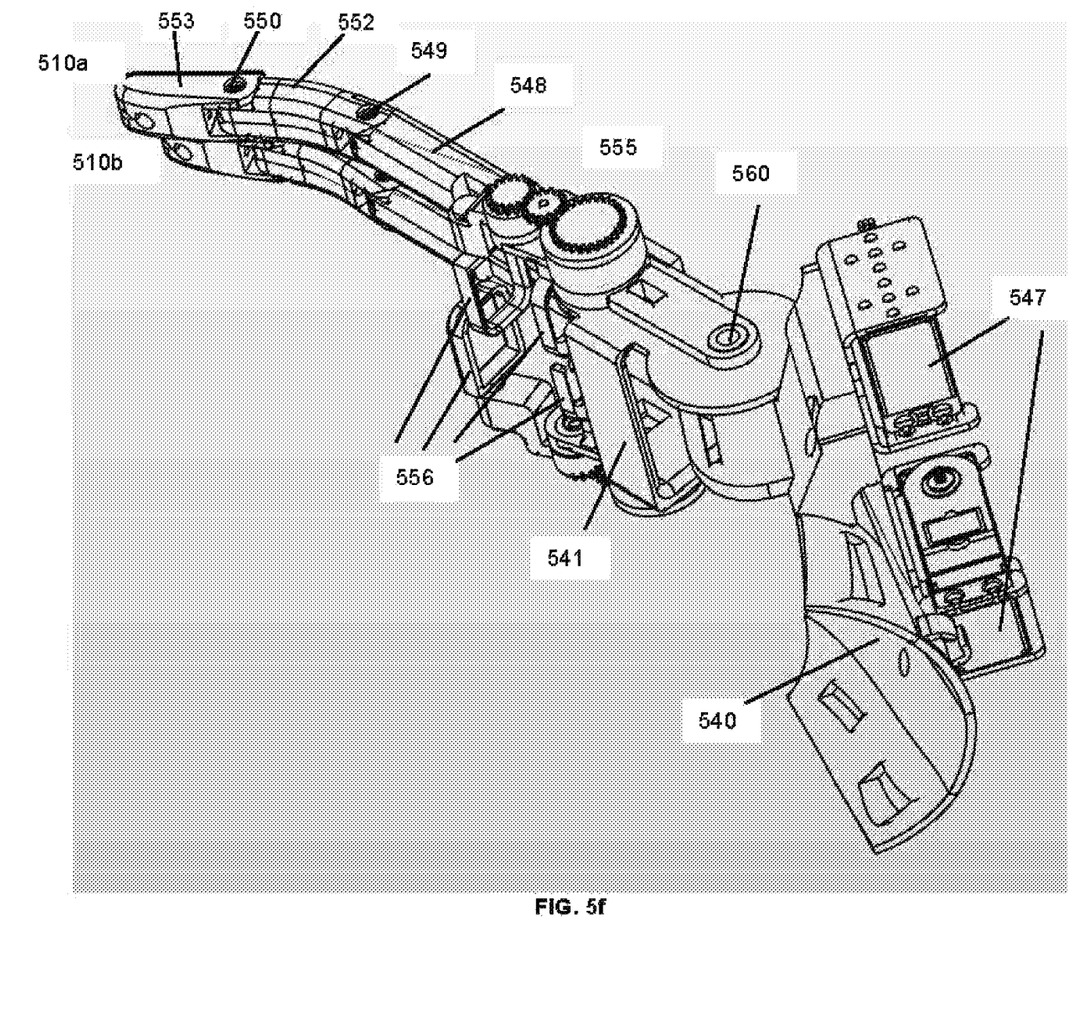
FIG. 5F is a bottom perspective view of the embodiment.

Referring to FIG. 5A, the proximal end of the digit extender includes hand mount 540 that is configured to fit on the back of the hand and positioning the finger mount portion 541 of the digit extender 510 over the user's finger or other appendage as the case may be, from the first, second or third joint or biologic articulation of the finger or other appendage. Hand mount 540 and finger mount 541 can be attached via articulation 560. Digital extender 510 has at least a first articulation/joint 549 and can include a second articulation/joint 550, or additional articulations or joints. In a particular aspect, the finger mount portion 541 of the device covers the distal two joints. In other aspects the digital extenders, finger mount portion, or the finger mount portion and digital extender covers all joints or articulations of the appendage (e.g., the finger). The fingertip or sensing portion of the appendage can be positioned on a haptic feedback element positioned in finger mount portion 541. In certain aspects the device or digit extender portion 510 has a fixed length. In other aspects the length of the device or digit extender portion 510 is adjustable and can be lengthened or shortened by the user. The length of the device or the digit extender 510 can be 1, 2, 3, 4, 5, 6, 7, 8, 9, 10 to 11, 12, 13, 14, 15, 16, 17, 18, 19, 20 inches long, including all values and ranges there between, as measured from proximal end to distal end. The digit extender 510 has a proximal mounting portion 551 that is configured to attach to finger mount portion 541, the length of digit extender 510 is measured from the beginning of the proximal portion 551 to the distal end of the digit extender 510 when full extended. In certain embodiments the device or digit extender 510 is 4 to 10 inches in length. The distal portion of digit extender 510 (i.e., that portion of 510 not including proximal portion 551) can be a circular, oval, triangular, square or a polygonal solid, matrix, or tube. The digit extender 510 need not maintain a consistent cross section and may constrict and expand in circumference or analogous dimension along its length. The proximal end of digit extender 510 is configured to receive the appendage (e.g., finger) inside the proximal end of the digit extender where it is secured once the appendage is appropriately positioned.

A distal portion (including a first distal portion 548, a second distal portion 552, and a tip portion 553) extends from the proximal portion (551) providing an extension of the finger. Digital extender 510 can have 1, 2, 3, or more articulation points connecting at various lengths along the device, e.g., connecting first distal portion 548 to second distal portion 552, or second distal portion 552 to tip portion 553. The articulation points can be configured to move in 1, 2, or 3 dimensions, with a first dimension being extension/retraction (x axis), a second dimension being up/down (y axis), and a third dimension being side to side (z axis). Proximal to the distal portion can be one or more articulation joints that provide sufficient flexibility to the distal portion of the device such that the distal portion can be directed over a required deflection range (180° or more) by the steering mechanism and can be directed to bend in any direction desired about the circumference of the distal portion. In certain aspects the user can select both the amount of bend or articulation and the direction of the bend. Tip portion 553 can have tactile or pressure sensing element(s) that are connected to a haptic feedback element and can transmit a sensed signal through connections to a haptic feedback element that interfaces with the user's finger or other appendage. A sensing element can use various mechanisms or combination of mechanisms for sensing, including but not limited to thermal, capacitive, hydraulic, or piezoelectric technologies that sense the environment at the distal end of the device (thus physically extending the sensory capability of the user) and translate a meaningful feedback signal to the user's finger that is connected to the feedback element. The connection between sensing element and feedback element can be a wired or a wireless connection.

In certain aspects the device can be moved and/or articulated by the user moving the appendage on which the device is placed or by other manipulation of the device, e.g., dials, gears, wires and such that can be manipulated by a user using an appendage not directly connected to the appendage positioned in the device. The device can also include actuators 547 that are mounted on the hand mount, as an example.

The device can include kinematic control system for the flexion and extension of the user's natural digit to control the flexion and extension of digit extender 510 or a portion thereof. The control system includes gears and mechanics (i.e., mechanism, which can also include pulleys, levers, strings, wires and the like) 555 configured to transfer the movement of a user to movement of the digit extender 510. The control system can include and one or more trigger 556 configured to allow manipulation of the extended digit 510 by moving the user's appendage. The mechanism and trigger are coupled to allow for movement of the digit extender. The user's appendage (e.g., finger) can be inserted into the finger mount and in position relative to trigger(s) to provide for manipulation of the device during use. The movement of the user's appendage can be captured or translated by a mechanical construct and translated to the digital actuation component. Constant tension may be applied above or below the digital actuation component to aid in overcoming forces for extension or flexion. This may be implemented by tension components such as actuators, pulleys, spring or elastic materials.

The distal tip can be configured for grasping, palpating, or moving structures (e.g., biological structures such as tissues or organs).

The device can be configured to be inserted in body openings (e.g., mouth, trachea, esophagus, vagina, rectum, etc.), or in surgical openings (e.g., during laparoscopy).

In certain embodiments, the device can be a fixed length device or an adjustable length device. In certain aspects the device is a telescopic device that can be adjusted before, during or before and during use.

The device can be manufactured from and/or coated with various materials or combinations of material. In certain aspects the material can include metallic materials including but not limited to stainless steels (SUS) such as SUS304, SUS316L, SUS420J2, and SUS 630, gold, platinum, silver, copper, nickel, cobalt, titanium, iron, aluminum, tin, various alloys such as a nickel-titanium (Ni—Ti) alloy, a nickel-cobalt (Ni—Co) alloy, a cobalt-chromium (Co—Cr) alloy, and a zinc-tungsten (Zn—W) alloy, metal-ceramic complexes, and the like. The material may be used alone, or two or more kinds among the above may be used concurrently. The device can also include polymer materials. Polymers include, but are not limited to polyamide resins such as Nylon 6, Nylon 11, Nylon 12, and Nylon 66 (all of which are registered trademarks), polyolefin resins including polyethylene resins such as Linear Low-Density Polyethylene (LLDPE), Low-Density Polyethylene (LDPE), High-Density Polyethylene (HDPE), and Ultra High Molecular Weight Polyethylene (UHPE or UHMWPE), or polypropylene resins, modified polyolefin resins, epoxy resins, urethane resins, diallyl phthalate resins (allyl resins), polycarbonate resins, fluororesins, amino resins (urea resins, melamine resins, and benzoguanamine resins), polyester resins, styrene resins, acrylic resins, polyacetal resins, vinyl acetate resins, phenol resins, vinyl chloride resins, silicone resins (silicon resins), polyether resins, polyimide resins, and the like. The polymer material may be used alone, or two or more kinds among the above may be concurrently used.

In certain embodiments the device can include other accessory devices such as a camera, clamp, scalpel, and the like.

The invention claimed is:

1. A medical device configured for extending dexterous reach and sensing of a finger comprising:
   a proximal attachment portion in the form of a hand mount, glove, wrist strap, or sleeve configured to receive and attach to a wrist or hand of a user;
   a distal portion comprising a distal sensor, the distal portion having a maximum diameter of 0.01 to 5 cm; and
   a digital extender portion having an extended length of 1 to 24 inches and a diameter of 0.01 to 5 cm that is configured to receive a finger of the user, the digital extender portion comprising a feedback element and at least one articulation, the digital extender portion is positioned between the distal portion and the proximal portion;
   wherein the feedback element is connected to or in communication with the sensor, the feedback element is configured to be connected to or in communication with the user's fingertip during use providing physical extension of sensory capabilities of the user's fingertip.

2. The device of claim 1, wherein the sensor is a thermal, capacitive, pneumatic, hydraulic, resistive, vibrational, and/or piezoelectric sensor, wherein sensory information is haptically communicated to the user's natural receptors when in use.

3. The device of claim 1, wherein the device is configured to translate movement of the user's finger to movement of the distal portion.

4. The device of claim 3, wherein the translation of movement is scaled at a scale of 1000:1 to 1:1 to 1:1000 proximal distance moved to distal distance moved.

5. The device of claim 1, wherein the device is made of materials that are capable of being sterilized.

6. The device of claim 1, wherein the device comprises 1, 2, 3, or 4 independent digital extender portions.

7. The device of claim 1, wherein the device comprises one digital extender portion.

8. The device of claim 1, wherein the device comprises 2 digital extender portions.

9. The device of claim 1, wherein the length of the digital extender portion is adjustable.

10. The device of claim 1, wherein the digital extender portion comprises at least two articulations.

11. The device of claim 1, further comprising a steering mechanism.

* * * * *